US005314444A

United States Patent [19]

Gianturco

[11] Patent Number: 5,314,444
[45] Date of Patent: * May 24, 1994

[54] ENDOVASCULAR STENT AND DELIVERY SYSTEM

[75] Inventor: Cesare Gianturco, Champaign, Ill.

[73] Assignee: Cook Incorporated, Bloomington, Ind.

[*] Notice: The portion of the term of this patent subsequent to Aug. 20, 2008 has been disclaimed.

[21] Appl. No.: 41,946

[22] Filed: Apr. 2, 1993

Related U.S. Application Data

[63] Continuation of Ser. No. 666,211, Mar. 7, 1991, abandoned, which is a continuation of Ser. No. 244,669, Sep. 14, 1988, Pat. No. 5,041,126, which is a continuation of Ser. No. 25,736, Mar. 13, 1987, Pat. No. 4,800,882.

[51] Int. Cl.$^5$ ............................................. A61M 29/02
[52] U.S. Cl. ................................... 606/195; 604/104
[58] Field of Search ................................. 606/191–200; 604/8, 96, 104; 623/1, 12, 900

[56] References Cited

U.S. PATENT DOCUMENTS

| | | |
|---|---|---|
| 3,278,176 | 10/1966 | Abolins .................................. 167/1 |
| 3,842,441 | 10/1974 | Kaiser .................................... 623/13 |
| 3,868,956 | 3/1975 | Alfidi et al. . |
| 4,140,126 | 2/1979 | Choudhury . |
| 4,183,102 | 1/1980 | Guiset . |
| 4,214,587 | 7/1980 | Sakura, Jr. . |
| 4,416,028 | 11/1983 | Erikson et al. . |
| 4,483,339 | 11/1984 | Gillis . |
| 4,503,569 | 3/1985 | Dotter . |
| 4,512,338 | 4/1985 | Balko et al. . |
| 4,553,545 | 11/1985 | Maass et al. . |
| 4,560,374 | 12/1985 | Hammerslag ......................... 604/49 |

(List continued on next page.)

FOREIGN PATENT DOCUMENTS

| | | |
|---|---|---|
| 0183372 | 6/1986 | European Pat. Off. . |
| 1205743 | 9/1970 | United Kingdom . |
| 2135585 | 9/1984 | United Kingdom . |

OTHER PUBLICATIONS

Palmaz et al., *Expandable Intrahepatic Portacaval Shunt Stents*, AJR 145:821–825, Oct. 1985.

(List continued on next page.)

*Primary Examiner*—Ralph Lewis
*Attorney, Agent, or Firm*—Woodard, Emhardt, Naughton, Moriarty & McNett

[57] ABSTRACT

A wire stent for insertion and expansion into a passageway comprises a plurality of curved sections that are formed into a generally circular configuration. Adjacent curved sections are joined by a bend or cusp, so that a series of alternating opposing loops are formed. The wire stent as formed has a cylindrical shape with a longitudinal opening through which a folded balloon catheter is inserted. The opposing loops are tightly contracted about the catheter so that the cylindrical shape has an overlapping region in which portions of adjacent loops longitudinally overlap. The loops are arranged so that when the balloon catheter is inflated, adjacent loops diverge circumferentially relative to each other, thereby decreasing the overlapping region while increasing the diameter of the cylindrical shape. As the diameter of the cylindrical shape increases, the wire stent contacts the surface of a passageway in which the stent is inserted.

In a method of the present invention, the wire stent is fabricated from a wire formed into a planar serpentine configuration. The wire is centered over a semi-cylindrical trough in a flat plate and then pressed into the trough by a forming bar so that a portion of the wire assumes the semi-cylindrical shape. A pulling tool, having a hook at one end, is engaged at the hook with the exposed loops of the serpentine configuration for pulling the exposed loops over the exposed portion of the forming bar to form a generally cylindrical shape from the wire. Once the wire is extracted from the trough and the forming bar is removed, a folded balloon catheter is inserted through the cylindrical shape and the wire is tightly pressed about the catheter.

8 Claims, 5 Drawing Sheets

U.S. PATENT DOCUMENTS

| | | |
|---|---|---|
| 4,562,596 | 1/1986 | Kornberg . |
| 4,577,631 | 3/1986 | Kreamer . |
| 4,580,568 | 4/1986 | Gianturco . |
| 4,641,653 | 2/1987 | Rockey ............................. 604/96 |
| 4,649,922 | 3/1987 | Wiktor . |
| 4,665,918 | 5/1987 | Garza et al. . |
| 4,665,918 | 5/1987 | Garza et al. . |
| 4,733,665 | 3/1988 | Palmaz . |
| 4,739,762 | 4/1988 | Palmaz . |
| 4,740,207 | 4/1988 | Kreamer . |
| 4,800,882 | 1/1989 | Gianturco ......................... 606/194 |
| 4,856,516 | 8/1989 | Hillstead . |
| 4,878,906 | 11/1989 | Lindemann et al. . |
| 5,041,126 | 8/1991 | Gianturco ......................... 606/195 |

OTHER PUBLICATIONS

Palmaz et al., *Expandable Intraluminal Graft: A Preliminary Study*, Radiology 156:73–77, 1985.

Palmaz et al., *Expandable Intraluminal Graft: A Feasibility Study*, Surgery 199–205, Feb. 1986.

Palmaz et al., *Atherosclerotic Rabbit Aortas: Expandable Intraluminal Grafting*, Radiology 160:723–726, 1986.

Roubin et al., "Early and Late Results of Intracoronary Arterial Stenting after Coronary Angioplasty in Dogs", *Circulation*, 76, No. 4, 891–897, Oct. 1987.

"Flexible Balloon-Expanded Stent for Small Vessels", *Radiology*, Jan. 1987, pp. 276–280, vol. 162, No. 1.

"Expandable Intraluminal Graft: A Preliminary Study"; *Radiology*, Jul. 1985; paper presented at 70th Scientific Assembly and Annual Meeting of the Radiology Society of North America.

"Percutaneous Endovascular Stents: An Experimental Evaluation"; Wright et al., *Radiology*, 156; 1985.

"Non Surgical Placement of Arterial Endoprostheses: A New Technique Using Nitinol Wire", Cragg et al., *Radiology*, 174:261–263, Apr. 1983.

"Transluminally-Placed Coilspring Endurtorial Tub Grafts", Dotter Investigative Radiology; Sep.–Oct. 1969.

"Radiology Follow-Up of Transluminally Inserted Vascular Endoprosthesis", *Radiology*, Sep. 1984, 152:659–663.

Dotter, C. T. et al., "Transluminal Expandable Nitonol Coil Stent Grafting", *Radiology*, Apr. 1983, 147:256–260.

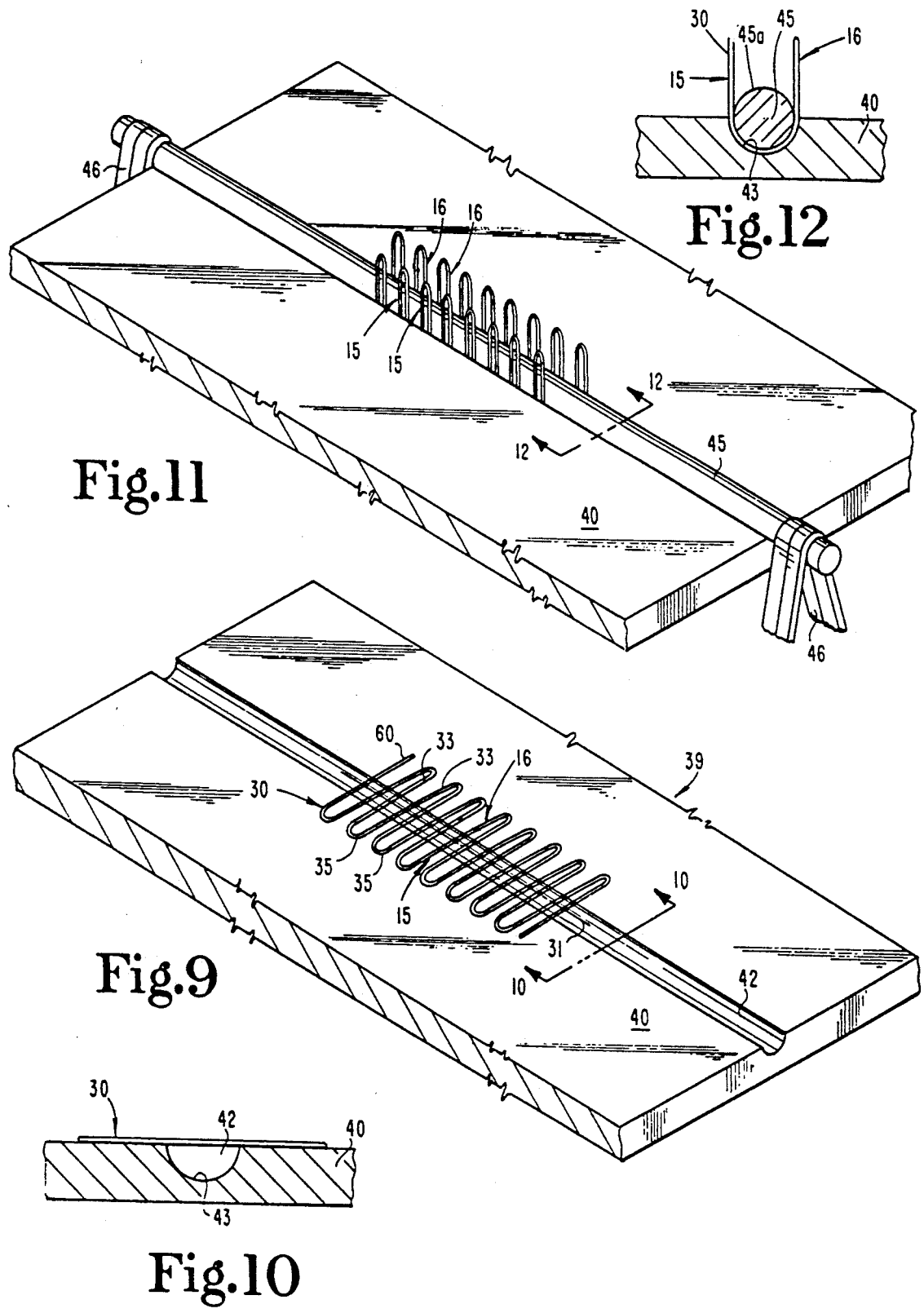

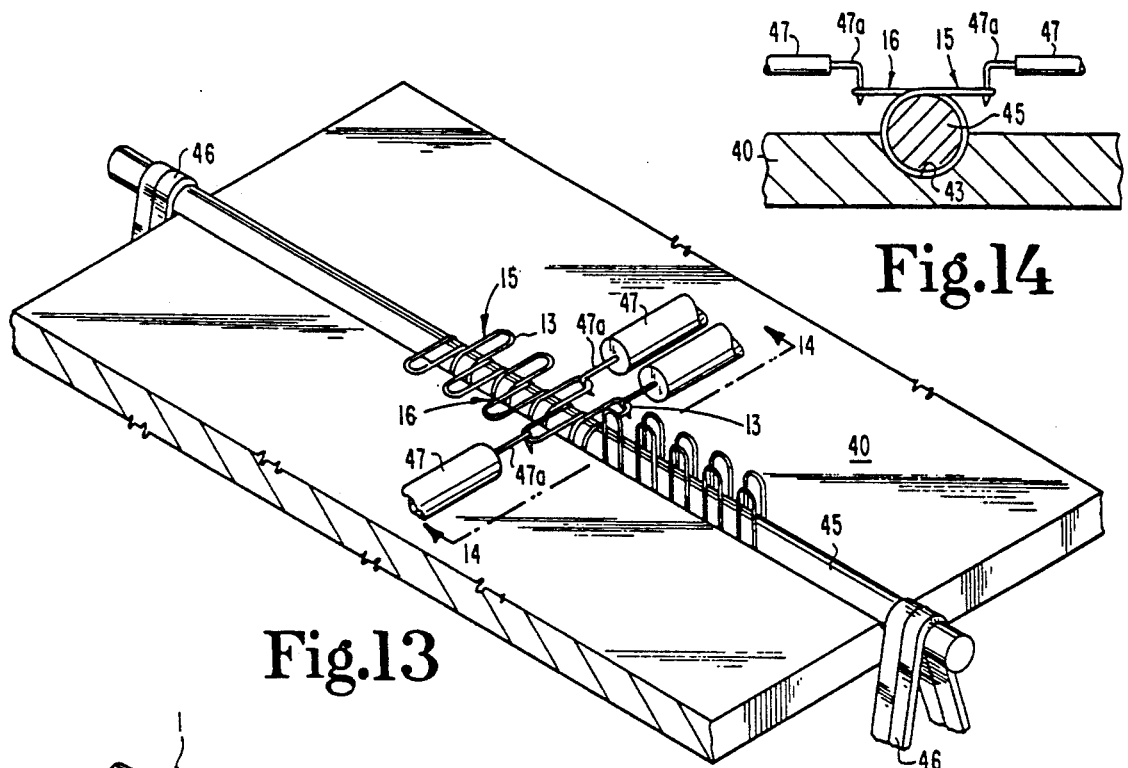
Fig.14
Fig.13
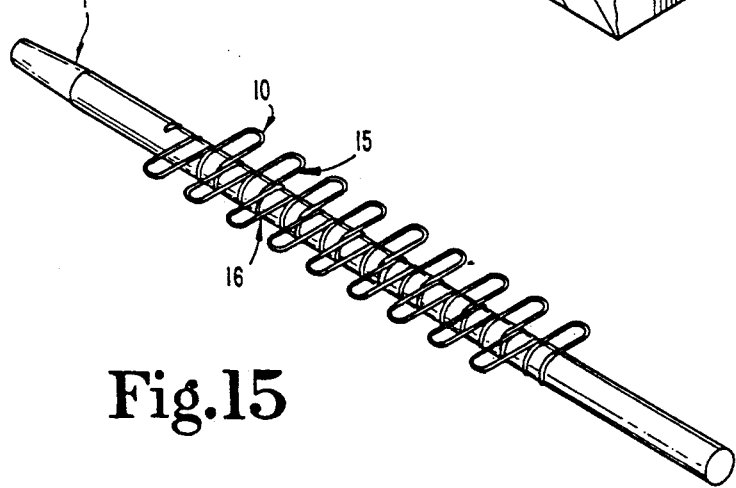
Fig.15

ENDOVASCULAR STENT AND DELIVERY SYSTEM

REFERENCE TO RELATED APPLICATIONS

This application is a continuation of Ser. No. 666,211 filed Mar. 7, 1991, now abandoned, which is a continuation of Ser. No. 244,669 filed Sep. 14, 1988, now U.S. Pat. No. 5,041,126 which is a continuation of Ser. No. 25,736 filed Mar. 13, 1987, now U.S. Pat. No. 4,800,882.

BACKGROUND OF THE INVENTION

1. Field of the Invention

This invention relates to stents and a method for inserting a stent.

2. Description of the Prior Art

It is desirable in various situations to provide means for expanding a constricted vessel or for maintaining an open passageway through a vessel. Such situations arise, for instance, after an angioplasty of a coronary artery. In these situations, wire stents are useful to prevent restenosis of the dilated vessel, or to eliminate the danger of occlusion caused by "flaps" resulting from intimal tears associated with angioplasty. Wire stents can also be used to reinforce collapsing structures in the respiratory and biliary tracts.

Typical of the wire stents of the prior art is the stent of Gianturco, U.S. Pat. No. 4,580,568, wherein the stent is compressed and encased in a sheath. The sheath is then positioned in the vascular system and the stent is held in position by a flat-ended pusher while the sheath is withdrawn. The zig-zag configuration of this particular stent allows it to expand in the passageway to hold the passageway open and enlarged.

Stents comprised of variously shaped spiral springs are described by Maass et al. in U.S. Pat. No. 4,553,545, and in *Radiology Follow-up of Transluminally Inserted Vascular Endoprosthesis: An Experimental Study Using Expanding Spirals*, Radiology, September 1984; 152: 659-663. Application of torque to the end of these spiral springs increases the number of coils while decreasing the stent diameter for insertion. Once inserted, an opposite torque is applied to the spiral springs causing the stent diameter to increase. Use of this type of stent requires a sophisticated coaxial cable to apply torque to the stent once it has been inserted into the vessel.

Dotter et al. reported the use of a prosthesis constructed of a thermal shape memory alloy which is passed into the passageway through a catheter. See, Dotter CT et al., *Transluminal Expandable Nitinol Coil Stent Grafting: Preliminary Report*, Radiology, April, 1983; 147: 259-260. This coil stent is compacted by cooling, inserted, and then heated in situ until the stent expands in the passageway. This stent is positioned within the vessel by a detachable positioning device capable of supplying electrical energy to heat the thermal coil.

Other references which may have relevance to the present invention are the following U.S. patents: Abolins, U.S. Pat. No. 3,278,176; Alfidi et al., U.S. Pat. No. 3,868,956; Simon, U.S. Pat. No. 4,425,908; and Sakura, Jr., U.S. Pat. No. 4,214,587.

Among the drawbacks of the prior art wire stents and expandable coil stents are that these stents are either difficult to produce or complicated to insert into a body passageway. Each of these stents requires the use of a complex device for insertion and expansion of the stent within the vessel. On the other hand, less complex wire stents lack the axial compliance to pass through a catheter that has any significant curves or bends. The present invention addresses each of these problems by providing a wire stent that is easy to produce, simple to install and capable of delivery around curves and bends in a vessel or passageway.

SUMMARY OF THE INVENTION

A stent comprising a wire formed into a serpentine configuration including a series of straight sections and a plurality of bends. The straight sections are joined by the bends to form a series of alternating loops. The serpentine configuration is formed into a cylindrical shape having a longitudinal axis, wherein the straight sections are bent into generally circular configurations surrounding and generally perpendicular to the longitudinal axis. Means are provided for expanding the circular configurations and, consequently, the cylindrical shape, comprising a balloon catheter. The balloon catheter is folded and received within the cylindrical shape and extends along the axis of the cylindrical shape. The straight sections are formed about the balloon catheter such that adjacent loops diverge circumferentially relative to each other as the balloon is inflated.

BRIEF DESCRIPTION OF THE DRAWINGS

FIG. 9 is a perspective view of a step of a method of the present invention showing a wire formed into a planar serpentine configuration and placed on a forming die.

FIG. 10 is a cross-sectional view of the forming die in FIG. 9 taken along line 10—10 and viewed in the direction of the arrows.

FIG. 11 is a perspective view of the wire pressed into a trough in the forming die by a forming bar.

FIG. 12 is a cross-sectional view of the forming die and forming bar of FIG. 11 taken along line 12—12 and viewed in the direction of the arrows.

FIG. 13 is a perspective view similar to FIG. 11 and showing the loops of the serpentine configuration pulled over the exposed portion of the forming bar by pulling tools.

FIG. 14 is a cross-sectional view of the forming die and forming bar in FIG. 13 taken along line 14—14 and viewed in the direction of the arrows.

FIG. 15 is a perspective of a balloon catheter inserted through a generally cylindrical opening formed by the wire in one step of the present method.

DESCRIPTION OF THE PREFERRED EMBODIMENT

Figures 1, 2:
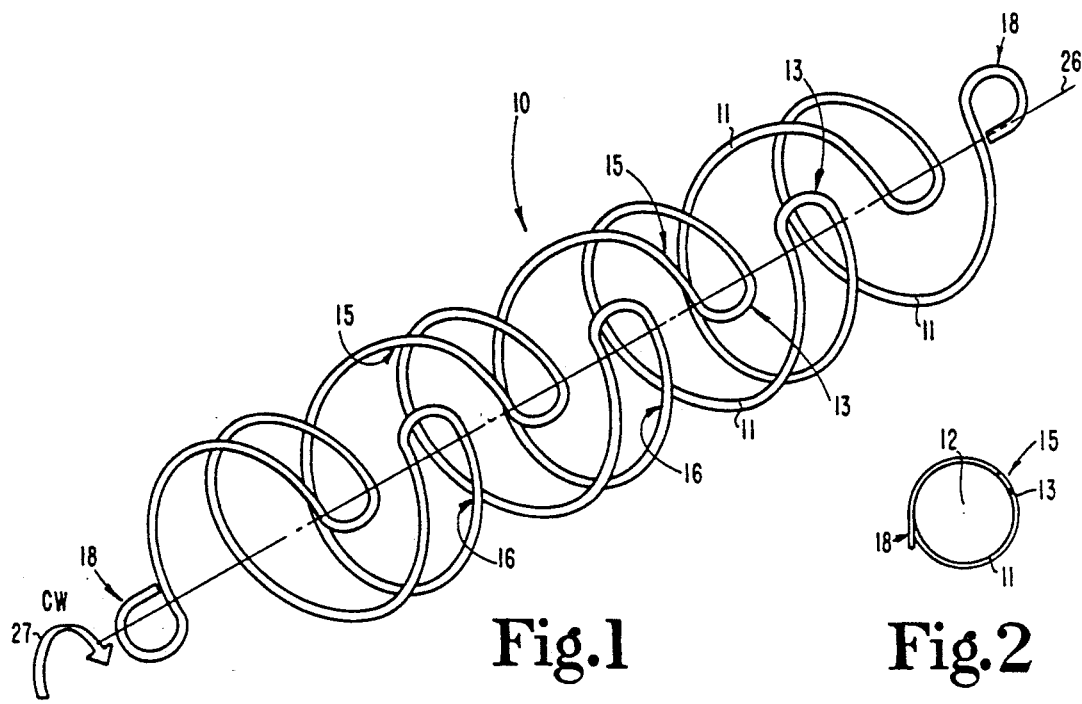
FIG. 1 is a perspective view of a wire stent of the present invention.
FIG. 2 is an end view of the wire stent of FIG. 1.

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Referring to FIG. 1, a wire stent 10 is shown as having a longitudinal axis 26. The stent comprises a plurality of curved sections 11 that are situated generally perpendicular to the axis 26. Adjacent curved sections 11 are joined by bends or cusps 13. A loop 18 is formed at each free end of the wire stent 10 in order to shield the wire end. The curved sections 11 are formed into a circular configuration, as shown in the end view of FIG. 2, so that the stent 10 has a cylindrical opening 12 formed therein.

The curved sections 11 and cusps 13 form a series of alternating clockwise and counter-clockwise loops 15 and 16, respectively. The clockwise direction relative to the axis 26 has been arbitrarily selected and is noted by the heavy arrow 27 in FIG. 1. In the contracted condition of the stent 10, these loops 15 and 16 overlap longitudinally, as demonstrated by the overlap region 20 shown in FIG. 3. Thus, the overlap region 20 gives the appearance that the stent is a continuous circular ring when viewed from an end, although when viewed as in FIGS. 1 or 3 it is apparent that the cylindrical shape of the stent 10 is discontinuous. The importance of this feature is illustrated by a comparison of FIGS. 3 and 4.

Figure 3:
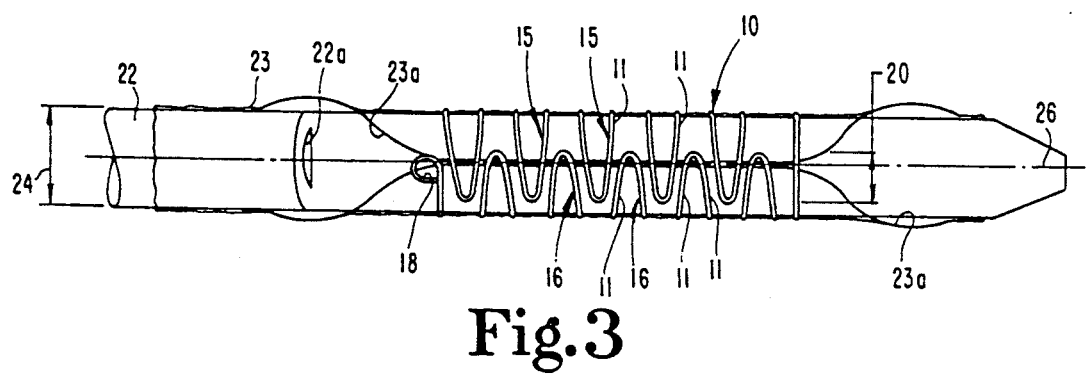
FIG. 3 is a side view of the wire stent of FIG. 1 engaged around a folded balloon catheter and shown in the contracted condition.
Figure 4:
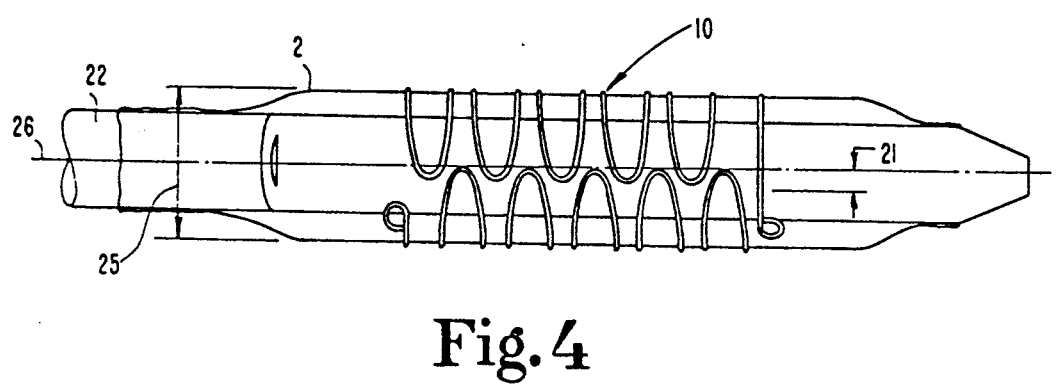
FIG. 4 is a side view of the wire stent and balloon catheter of FIG. 3, shown in the expanded condition.

In FIG. 3, the stent 10 is shown secured around a catheter 22, which has an inflatable balloon 23 adhered thereon surrounding a feed orifice 22a in the catheter. The balloon used in this embodiment is a folded balloon in which flaps 23a of the balloon 23 are folded over the catheter 22, as shown in FIG. 3. The folded flaps 23a allow the balloon 23 to inflate to a specific diameter without excessively stretching the balloon material and risking a rupture of the balloon.

The stent is compressed about the catheter 22 and balloon 23 so that it assumes a contracted outer diameter 24, which is calibrated to allow insertion into a particular body passageway. The clockwise loops 15 and counter-clockwise loops 16 overlap in the region 20, and the spring stiffness of the wire keeps the stent in this position during insertion. The stent 10 remains in tight contact with the catheter 22 even as the assembly is delivered around curves and bends in a body passageway.

After the catheter and stent are fully inserted into the passageway, the balloon 23 is inflated to a diameter 25, which is calibrated to force the stent 10 into contact with the passageway inner surface and, at least in some cases, to expand the passageway. As the balloon is inflated, the clockwise and counter-clockwise loops 15 and 16 diverge circumferentially until the longitudinal overlap between loops is reduced to the region 21, shown in FIG. 4. Thus, the effective diameter of the stent 10 relative to the longitudinal axis 26 is increased without thermal expansion or application of torsional forces to the stent, as suggested in the prior art.

In the best mode of the invention, the wire comprising the stent 10 is made of a malleable material, preferably from the group comprising annealed stainless steel, tungsten and platinum. This malleable material is sufficiently deformable to allow the loops 15 and 16 to diverge due to radially outward pressure applied by inflation of the membrane that comprises the standard balloon catheter. Because the stent material is plastic, rather than elastic, the stent retains the enlarged diameter after the balloon 23 is deflated and the catheter 22 removed. However, the material has sufficient strength and stiffness to avoid the stent being displaced on the balloon during insertion and to avoid the loops 15 and 16 being forced into an overlying relation. Further, the stent has sufficient strength and stiffness to allow it to maintain its position in the passageway and to resist being dislodged after the catheter 22 has been removed and the balloon is no longer stabilizing the stent. One example of a suitable wire has an outer diameter of 0.0018 inches and is stainless steel AISI 316 alloy.

It is desirable that the overlap region 20 in the contracted condition be sufficiently large so that the stent has a high contact area with the catheter, providing additional protection against the stent becoming dislodged while the assembly is inserted. In the expanded condition, the overlap region 21 should be sufficiently large to provide continuous circumferential support for the passageway in which the stent is inserted. In one example of the invention, the overlaying region 20 extends almost 360° circumferentially. For clarity, the illustrated embodiment shows the overlap 20 to be substantially less.

Figure 5:
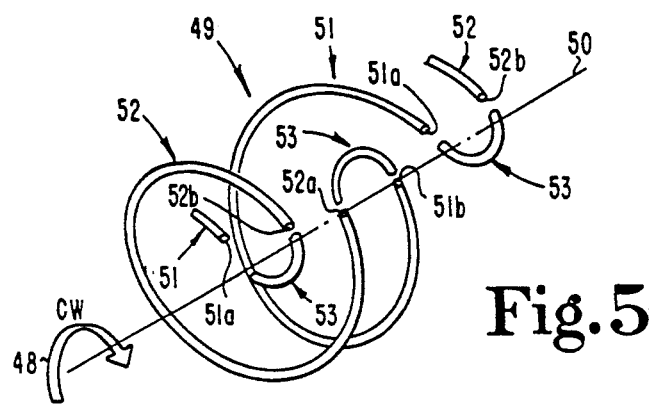
FIG. 5 is a fragmentary exploded view of a portion of a wire stent of FIG. 1.

It can be observed that applicant's preferred embodiment can be dissected into single coil helical sections. FIG. 5 is an exploded view of a wire stent 49 having a longitudinal axis 50. The clockwise direction, according to a right-hand rule, is denoted by the heavy arrow 48 about the axis 50. The stent 49 comprises a series of alternating single coil clockwise helical sections 51 and single coil counter-clockwise helical sections 52. The helical sections 51 and 52 have forward ends 51a and 52a, and aft ends 51b and 52b, respectively. The adjacent helical sections are joined by cusps 53, with the forward end of one helical section being connected to the aft end of the next helical section. Thus, end 51a of the clockwise helical section 51 is joined to end 52b of the counter-clockwise helical section 52, while end 52a is connected to end 51b.

Figure 6:
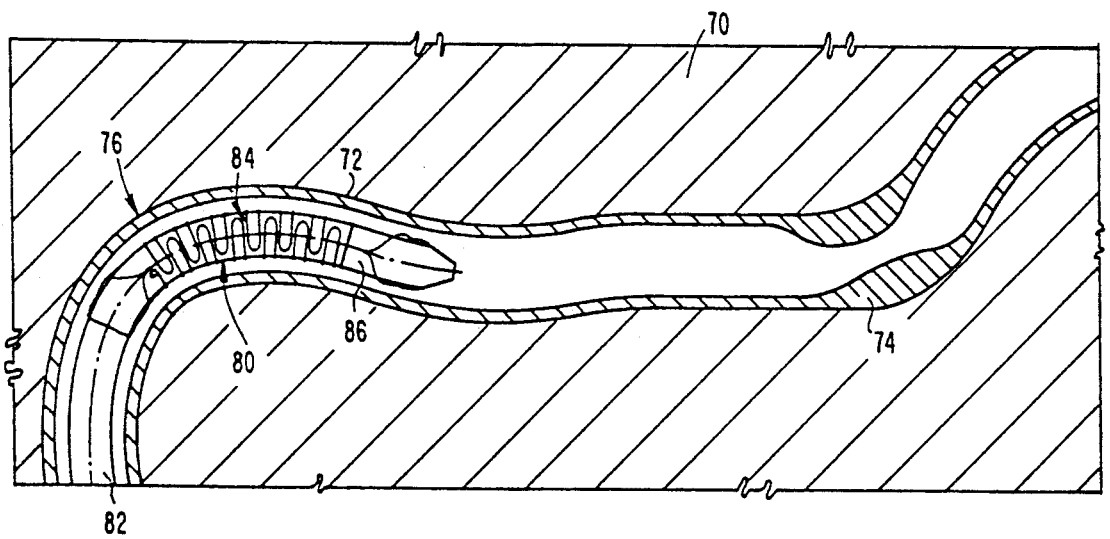
FIG. 6 is a cutaway view of a body cavity with the wire stent and balloon catheter situated in a curve in the cavity.

In a method of using the stent of the present invention, a stent and balloon catheter assembly 80 is inserted into a passageway 72, such as an artery, in a patient's body 70, as shown in FIG. 6. The assembly 80 is in the deflated configuration as it is maneuvered around the curve 76 in the passageway 72. The stiffness of the catheter 82 allows the assembly 80 to follow the curve 76, while the strength and stiffness of the stent 84 keeps it tightly engaged on the catheter balloon 86 during insertion. The passageway has an occlusion 74 situated at another bend in the passageway.

Figure 7:
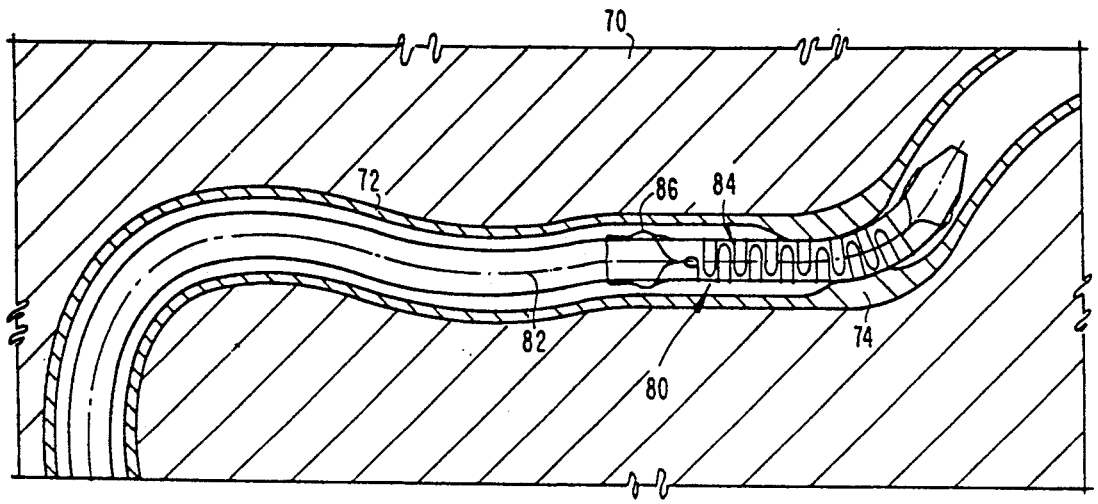
FIG. 7 is the cutaway view similar to FIG. 6 with the stent and balloon catheter situated within the cavity adjacent an occlusion in the cavity.
Figure 8:
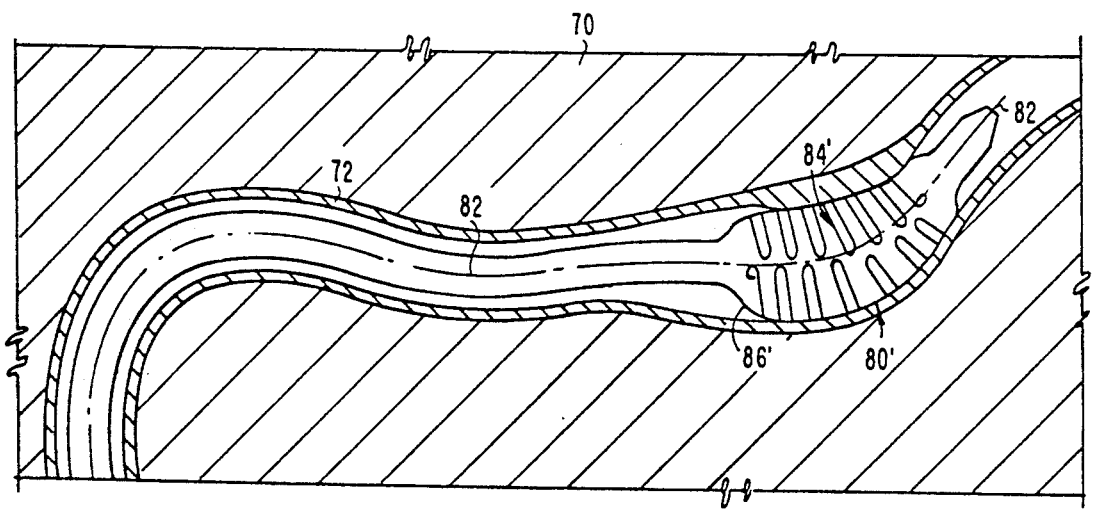
FIG. 8 is the cutaway view of FIG. 7, shown with the balloon catheter inflated and with the stent in contact with the cavity wall to remove the occlusion.

In FIG. 7, the stent and balloon catheter assembly 80 is shown fully inserted into the passageway 72 so that the stent 84 and balloon 86 are situated directly adjacent the occlusion 74 and following the curve of the passageway. The assembly is shown in the expanded configuration 80' in FIG. 8, in which the balloon 86' is inflated and the wire stent 84' expanded to contact and enlarge the passageway 72. The expansion is exaggerated in FIG. 8 for clarity. The assembly is expanded a sufficient amount to remove the occlusion 74 (FIG. 7) and open the passageway. The balloon is then deflated and the catheter removed, leaving the stent to hold the passageway open.

The method of the present invention concerns a process for fabricating a stent. Referring to FIG. 9, wire 30 is bent into a planar serpentine shape. The shape includes a series of straight sections 33 joined by bends or cusps 35. After the forming procedure has occurred, the straight sections 33 become curved sections 11, and cusps 35 become cusps 13. Also, the portions of wire 30 on either side of the centerline 31 become the clockwise and counter-clockwise loops 15 and 16, as designated in FIG. 9. Free end 60 can be formed into a loop, such as loop 18 in FIG. 1.

A forming die 39 comprises a flat plate 40 having a straight trough 42 formed therein. In the cross-sectional view of FIG. 10, it is seen that the trough 42 has a semi-circular surface 43. The wire 30 is placed flat upon the plate such that the centerline 31 is coincident with the centerline of the trough 42.

The wire 30 is pressed into the trough 42 and against the semi-circular surface 43 using a forming bar 45, as shown in FIGS. 11 and 12. The forming bar 45 is held in place by elastic bands 46. The ends of the loops 15 and 16 project upwardly or outwardly from the trough 42 and above the surface of the flat plate 40. In the next step of the present method, pulling tools 47 are used to pull the loops 15 and 16 over the exposed surface 45a (FIG. 12) of the forming bar 45, as shown in FIGS. 13 and 14. Hooks 47a at the end of pulling tools 47 engage the cusps 13 of the loops 15 and 16 during this pulling step. Next, the partially formed stent is removed from the plate 40 by lifting the forming bar away from the plate. The bar 45 is removed, leaving the configuration of the partially formed stent at this point is as shown in FIG. 15.

The balloon catheter 22 is inserted through the longitudinal cylindrical opening 12 in the stent 10, as shown in FIG. 15, and the ends of the loops 15 and 16 are pressed into contact with the catheter, as shown in FIG. 3. As mentioned, when the loops 15 and 16 are in their final overlapping position, it is preferred that they overlap a substantial amount. In one example of the invention, this overlap 20 (FIG. 3) is about 360 degrees. The balloon catheter used could be of various designs, such as the design shown in the patent to William A. Cook, U.S. Pat. No. 4,637,396, or as available from Cook, Inc. of Bloomington, Ind., under their catalogue number OMG 4.0-4.5 and 5.3FR catheter.

While the invention has been illustrated and described in detail in the drawings and foregoing description, the same is to be considered as illustrative in character, it being understood that only the preferred embodiment has been shown and described.

What is claimed is:

1. A stent comprising:
   a malleable wire formed into a serpentine pattern including a plurality of wire segments joined in a series by a plurality of bends;
   said serpentine pattern being wrapped about a longitudinal axis to define a hollow cylinder;
   said hollow cylinder having a first diameter and at least a portion of said hollow cylinder being inelastically deformable from said first diameter to a second expanded diameter; and
   means, disposed within said hollow cylinder, for inelastically expanding said portion from said first diameter to said second expanded diameter.

2. The stent of claim 1 wherein said means for expanding is a balloon catheter.

3. The stent of claim 2 having a length defined by said serpentine pattern along said longitudinal axis and wherein the stent includes means for maintaining said length substantially constant when said stent is expanded from said first diameter to said second expanded diameter.

4. The stent of claim 3, wherein said means for maintaining said length includes said plurality of wire segments oriented substantially perpendicular to said longitudinal axis between said bends.

5. The stent of claim 2 wherein said bends are U-shaped bends.

6. The stent of claim 5 wherein successive U-shaped bends open in alternating directions.

7. The stent of claim 6 wherein the stent has a longitudinal axis and said U-shaped bends are distributed substantially uniformly along said longitudinal axis.

8. The stent of claim 7 wherein the stent is longitudinally flexible relative to a curved body passageway such that said longitudinal axis assumes a curved shape when positioned in a curved body passageway.

* * * * *